United States Patent [19]

Murai et al.

[11] 4,098,892

[45] Jul. 4, 1978

[54] NICOTINAMIDO-S-TRIAZINES

[75] Inventors: Hiromu Murai, Otsu; Katsuya Ohata, Uji; Kenji Sempuku, Suita; Yoshiaki Aoyagi, Kyoto; Fusao Ueda, Shiga, all of Japan

[73] Assignee: Nippon Shinyaku Co., Ltd., Kyoto, Japan

[21] Appl. No.: 769,948

[22] Filed: Feb. 18, 1977

[30] Foreign Application Priority Data

Mar. 29, 1976 [JP] Japan .................................. 51-34949

[51] Int. Cl.² .................. A61K 31/53; C07D 251/48; C07D 251/70

[52] U.S. Cl. .................................. 424/249; 544/198; 544/209

[58] Field of Search ................. 544/198, 209; 424/249

[56] References Cited

U.S. PATENT DOCUMENTS 2,822,347  2/1958  Wohnsiedler ........................ 544/198

Primary Examiner—John M. Ford
Attorney, Agent, or Firm—Jacobs & Jacobs

[57] ABSTRACT

The mono-, bis- and trisnicotinoyl derivatives of melamine and the corresponding mono- and bisnicotinoyl derivatives of benzoguanamine demonstrate anti-ulcer and diuretic activity. A representative embodiment is 2-nicotinamido-4,6-diamino-s-triazine.

11 Claims, No Drawings

NICOTINAMIDO-S-TRIAZINES

DETAILED DESCRIPTION

The present invention pertains to compounds selected from the group consisting of the class of nicotinamido-s-triazines represented by the formula:

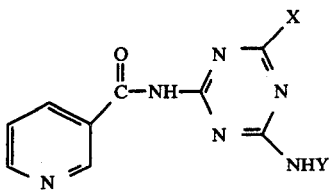

wherein
X is amino, phenyl or nicotinamido; and
Y is hydrogen or nicotinoyl, and the acid addition salts thereof.

The compounds of the present invention demonstrate strong anti-ulcer effects and diuretic activity and are of low toxicity.

The compounds are conveniently obtained by the reaction of melamine (2,4,6-triamino-s-triazine) or benzoguanamine (2,4-diamino-6-phenyl-s-triazine) and a reactive derivative of nicotinic acid, as for example acid chlorides, dichlorophosphoric acid anhydride, sulfonic acid anhydride, mixed carbonic acid anhydrides such as ethoxycarbonic acid anhydride, nitrophenyl esters, carbodiamides, and the like. When mixtures of the mononicotinamido and polynicotinamido derivatives are obtained, the individual compounds can be immediately separated through conventional methods such as fractional crystallization, chromatography and the like.

As indicated, the present invention also pertains to the physiologically acceptable nontoxic acid addition salts of these basic compounds. Such salts include those derived from organic and inorganic acids such as, without limitation, hydrochloric acid, hydrobomic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The anti-ulcer effects and diuretic acticity of these compounds can be observed in recognized laboratory models. For example, diuretic activity can be observed in the saline loaded rat measuring the increase in the ratio of urine excretion. Upon the administration for example of 20 mg/kg i.p. of 2,4,6-tris(nicotinamido)-s-triazine, the ratio of increased excretion is 1.22 whereas upon administration of 50 mg/kg i.p. of 2-amino-4-nicotinamido-6-phenyl-s-triazine, the ratio is 3.06.

The anti-ulcergenic activity can likewise be observed in recognized models such as for example the Shay rat in which at a dosage of 20 mg/kg i.p., the following values for ulcer inhibition can be observed.

Table

| X | Y | Ulcer Inhibition Rate |
|---|---|---|
| Amino | Hydrogen | 97% |
| Nicotinamido | Nicotinoyl | 93% |
| Phenyl | Hydrogen | 46% |
| Phenyl | Nicotinoyl | 36% |
| Amino | Nicotinoyl | 91% |

Generally satisfactory responses for both indications are observed in humans and other animals in dosage ranges of from 1 to 100 mg/kg. The diuretic properties of thse compounds make them useful in the treatment of conditions where such action is desired, as for example in hypertension, whereas by reason of their anti-ulcergenic activity, the compounds can be used both prophylactically and therapeutically in the treatment of gastric ulcers.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The following examples will serve to further typify the nature of this invention but should not be construed as a limitation thereof, the invention being defined solely by the appended claims.

EXAMPLE 1

4.9 g of melamine and 17 g of nicotinic acid anhydride are refluxed in 300 ml of pyridine with stirring for 3 hours. After cooling, the pyridine is removed by evaporation to dryness under vacuum and the residue is washed with 3% aqueous potassium carbonate and then with water. The residue is fractionated and recrystallized from methanol to yield 2-nicotinamido-4,6-diamino-s-triazine [monomicotinoylmelamine], melting point 252° – 254° C in a yield of 2.4 g and 2,4-bis(-nicotinamido)-6-amino-s-triazine [dinicotinoylmelamine], melting point 265° – 270° C (dec) in a yield of 0.15 g.

EXAMPLE 2

1.33 g of melamine and 10 g of nicotinic acid anhydride are mixed and pulverized and then heated at 150° C for 20 minutes. After cooling, the mixture is added to 300 ml of water and boiled to remove the soluble matter. The residue is recrystallized from methanol to obtain 2,4,6-tris(nicotinamido)-s-triazine [trinicotinoylmelamine], melting point 276° – 278° C in a yield of 1.52 g.

EXAMPLE 3

1.3 g of melamine and 2.5 g of nicotinic acid are dissolved in 80 ml of pyridine, and 3.1 g of phosphoryl chloride are then added dropwise to the mixture with stirring. After continuing agitation for 3 hours, the mixture is processed as described in Example 1 to yield 520 mg of 2,4,6-tris(nicotinamido)-s-triazine [trinicotinoylmelamine] and 130 mg of 2-nicotinamido4,6-diamino-s-triazine [mononicotinoylmelamine].

EXAMPLE 4

5.7 g of benzoguanamine and 4.0 g of nicotinic acid are dissolved in 300 ml of pyridine, and this solution is stirred with 5.0 g of phosphoryl chloride at room temperature. After continuing agitation at 60° C for 2 hours, the pyridine is removed by evaporation to dryness under vacuum. The residue is washed with water and fractionated and recrystallized from a mixed solution of methanol and dioxane, to yield 2-amino-4-nicotinamido-6-phenyl-s-triazine [mononicotinoylbenzoguanamine], melting point, 240° – 242° C in a yield of 2.8 g, and 2,4-bis(nicotinamido)-6-phenyl-s-triazine [dinicotinoylbenzoguanamine], melting point, 131° – 133° C in a yield of 0.7 g.

EXAMPLE 5

1.9 g of benzoguanamine and 3.6 g of nicotinic acid chloride (or an equivalent amount of the hydrochloride) are dissolved in 70 ml of pyridine and heated at 60° C for 6 hours. The reaction mixture is processed as described in Example 4 to yield 0.17 g of 2-amino-4-nicotinamido-6-phenyl-s-triazine [mononicotinoylbenzoguanamine] and 1.2 g of 2,4-bis(nicotinamido)-6-phenyl-s-triazine [dinicotinoylbenzoguanamine].

EXAMPLE 6

1.9 g of benzoguanamine and 2.6 g of nicotinic acid are dissolved in 50 ml of pyridine and mixed with 2.2 g of chloroethyl carbonate. After heating the mixture at 60° C with agitation for 3 hours, it is processed as described in Example 4 to yield 1.3 g of 2,4-bis(-nicotinamido)-6-phenyl-s-triazine [dinicotinoylbenzoguanamine].

EXAMPLE 7

1.9 g of benzoguanamine and 2.6 g of nicotinic acid are dissolved in 50 ml of pyridine, and the mixture is further mixed with 2.5 g of methanesulfonyl chloride and agitated at 60° C for 3 hours. Following processing as described in Example 4, there is obtained 0.11 g of 2-amino-4-nicotinamido-6-phenyl-s-triazine [mononicotinoylbenzoguanamine] and 1.05 g of 2,4-bis(nicotinamido)-6-phenyl-s-triazine (dinicotinoylbenzoguanamine).

What is claimed is:

1. A compound selected from the group consisting of a nicotinamido-s-triazine of the formula:

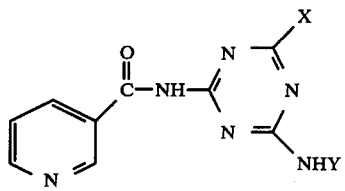

wherein
X is amino, phenyl or nicotinamido; and
Y is hydrogen or nicotinoyl, and the acid addition salts thereof.

2. A compound according to claim 1 wherein X is amino.

3. A compound according to claim 1 wherein X is phenyl.

4. A compound according to claim 1 wherein X is nicotinamido.

5. A compound according to claim 1 which is 2-nicotinamido-4,6-diamino-s-triazine.

6. A compound according to claim 1 which is 2,4-bis(nicotinamido)-6-amino-s-triazine.

7. A compound according to claim 1 which is 2,4,6-tris(nicotinamido)-s-triazine.

8. A compound according to claim 1 which is 2-amino-4-nicotinamido-6-phenyl-s-triazine.

9. A compound according to claim 1 which is 2,4-bis(nicotinamido)-6-phenyl-s-triazine.

10. The method of achieving an anti-ulcer effect in humans and other animals which comprises administering to a human or animal in need thereof an anti-ulcer effective amount of a compound according to claim 1.

11. A pharmaceutical composition comprising an anti-ulcer effective amount of a compound according to claim 1 in combination with a pharmaceutical carrier.

* * * * *